United States Patent [19]

Morita et al.

(10) Patent No.: US 7,212,109 B2
(45) Date of Patent: May 1, 2007

(54) HYGIENIC INPUT DEVICE FOR MEDICAL INFORMATION SYSTEMS

(75) Inventors: Mark M. Morita, Arlington Heights, IL (US); Steven L. Fors, Chicago, IL (US); Khal A. Rai, Round Lake, IL (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 47 days.

(21) Appl. No.: 10/779,235

(22) Filed: Feb. 13, 2004

(65) Prior Publication Data

US 2005/0179538 A1 Aug. 18, 2005

(51) Int. Cl.
*G08B 1/08* (2006.01)

(52) U.S. Cl. ............................. 340/539.12; 340/539.1; 340/691.6; 750/3; 345/156

(58) Field of Classification Search .......... 340/539.12, 340/539.1, 573.1, 691.1, 691.6; 379/21; 750/3; 345/156, 168, 169, 173
See application file for complete search history.

(56) References Cited

U.S. PATENT DOCUMENTS 5,561,446 A * 10/1996 Montlick .................... 345/173

| 6,526,304 | B1 | 2/2003 | Patel et al. |
| 6,611,253 | B1 * | 8/2003 | Cohen .......................... 345/168 |
| 6,614,422 | B1 | 9/2003 | Rafii et al. |
| 6,650,318 | B1 | 11/2003 | Arnon |

OTHER PUBLICATIONS www.vbk.co.in.
www.bluetooth.org.

* cited by examiner

*Primary Examiner*—Daryl C Pope
(74) *Attorney, Agent, or Firm*—McAndrews, Held & Malloy, Ltd.; Peter J. Vogel; Michael A. Dellapenna

(57) ABSTRACT

A system for hygienic input of data into a medical information system is provided. In one embodiment of the system, a computer terminal, a mobile wireless input tray, a mobile wireless interactive visual display system, and a wireless headset are used. During a medical procedure, the mobile input tray, the mobile display system, and the wireless headset may be positioned in an operating room near a surgeon or other medical practitioner. The mobile input tray, the mobile display system, and the wireless headset may be used to access patient medical information through the computer terminal. The mobile input tray, the mobile display system, and the wireless headset communicate amongst and between each other through wireless communication links. The mobile input tray, the mobile display system, and the wireless headset communicate with the computer terminal through wireless communication links.

4 Claims, 5 Drawing Sheets

HYGIENIC INPUT DEVICE FOR MEDICAL INFORMATION SYSTEMS

CROSS REFERENCE TO RELATED APPLICATIONS

Not Applicable

STATEMENT REGARDING FEDERALLY SPONSORED RESEARCH OR DEVELOPMENT

Not Applicable

REFERENCE TO MATERIALS ON COMPACT DISC

Not Applicable

BACKGROUND OF THE INVENTION

The present invention generally relates to input devices for medical information systems. More particularly, the present invention relates to hygienic input devices for medical information systems.

Medical information systems such as picture archiving and communications systems (PACS) are used to store patient information. The patient information stored in a PACS may include various types of information such as patient medical history, imaging data, test results, and diagnosis information. Because the various types of information may be gathered at various times and in a variety of locations, the PACS system provides a convenient centralized storage location that provides access to medical information from numerous locations.

One example of the numerous locations where patient information stored in a medical information system may be accessed from is within or near operating rooms. During the course of surgery, medical personnel may desire to access patient information stored in a medical information system. For example, medical personnel may desire to view ultrasound or CT images taken of a patient's anatomy. By accessing images of a patient's anatomy in close temporal proximity to the time of surgery, medical personnel may find it easier to navigate a patient's anatomy and more quickly treat a patient's illness.

Alternatively, medical personnel may desire to enter new information into the system regarding a currently ongoing medical procedure. For example, medical personnel may enter a patient's name and other information associated with an image being obtained during an ongoing invasive or non-invasive medical procedure. Similarly, medical personnel may enter diagnostic or treatment information.

In typical systems, medical personnel interact with a medical information system such as a PACS through a local computer terminal. The local computer terminal typically includes devices such as a keyboard or mouse. Medical personnel enter data into the computer terminal by typing on the keyboard or manipulating the mouse.

Entering data using the keyboard and mouse utilized with existing systems requires medical personnel to physically contact the keyboard or mouse. Because the keyboard and mouse may have bacteria and other germs on their surfaces, physical contact between medical personnel and either the keyboard or mouse exposes medical personnel to the bacteria and other germs. Such exposure is commonly referred to as a violation of the integrity of an individual's sterile field. To remedy violations of a sterile field, medical personnel that have come into contact with a non-sterile object must re-sterilize.

For medical personnel in an operating room, re-sterilizing usually includes re-scrubbing and new gloves. Consequently, each time medical personnel access a typical medical information system, in or near an operating room, by typing on a keyboard or manipulating a mouse, the medical personnel are forced to re-scrub their hands and put on new gloves. Re-scrubbing and re-gloving may become cumbersome and time consuming, and may discourage medical personnel from accessing medical information systems.

Consequently, it may be preferable to have a system where medical personnel do not have to physically contact unsterile or contaminated input devices to access the medical information system. In addition, it may be preferable to have a medical information system where medical personnel do not violate the integrity of the sterile field when interacting with the medical information system.

Also, computer terminals connected to medical information systems are sometimes installed in a fixed location like a room with a desk. To interact with the computer terminal, medical personnel have to trek to the location where the computer terminal is located. With computers limited to fixed locations, a computer terminal may not be conveniently located and accessible during a medical procedure.

To reduce the inconvenience of having to walk to where a computer is located, some medical information systems use a computer terminal that is installed on a portable structure. Like the computer terminal installed in a fixed location, the computer terminal installed on the portable structure is connected to a power source through a cord plugged into a standard floor or wall outlet. Similarly, communication between the computer terminal installed on the portable structure and the medical information system is conducted through a communication wire run between a communication port on the computer terminal and a communication terminal in a wall or floor jack.

While the physical connections provided by the power cord and communication wire provide the operability of the computer terminal installed on the portable structure, the physical connections also limit the operability of the computer terminal. For example, ease of use of the computer terminal is hampered by the presence of the power cord and communication wires. First, the lengths of the power cord and communication wires limit the range of movement of the portable structure. Second, medical personnel must maneuver the cord and wires in order to position the portable structure and such maneuvering may require medical personnel to violate the integrity of their sterile field by touching the wires. Third, the cord and wires present a tripping hazard for medical personnel. Fourth, unplugging the cord and communication wire to move the computer terminal may require rebooting the terminal.

Consequently, it may be preferable to have a portable computer terminal that operates without having a power cord plugged into a standard wall or floor outlet. In addition, it may be preferable to have a portable computer terminal that operates without having a communication wire running between a communication port on a computer terminal and a communication terminal located on a floor or wall.

BRIEF SUMMARY OF THE INVENTION

A preferred embodiment of the present invention provides a system for hygienic input of data into a medical information system. The system may include a computer terminal, a mobile wireless input tray, a mobile wireless interactive visual display system, and/or a wireless headset. During a medical procedure, the mobile input tray, the mobile display system, and/or the wireless headset may be positioned in an operating room near a surgeon or other medical practitioner. The mobile input tray, the mobile display system, and the wireless headset may be used to access patient medical information through the computer terminal.

The local computer terminal is linked with a remote data storage unit through a communication data port. The remote data storage unit stores patient medical information so that it may be accessed from multiple locations. A user may wear the wireless headset and speak into the headset to transmit data to the computer terminal. A user may also listen to data transmitted from the computer terminal to the headset through speakers in an earpiece of the headset. The wireless headset transmits data to and from the computer terminal through a wireless communication link.

The mobile input tray may be positioned near a surgeon or medical practitioner and used to transmit data to the computer terminal through a wireless communication link. To transmit data to the local computer terminal from the mobile input tray, a user may type on a virtual keyboard projected onto a surface of the mobile tray. A sensor detects the keystrokes typed on the virtual keyboard and data representing the keystrokes is transmitted to the local computer through a wireless communication link. In addition to a virtual keyboard, an operating room mouse may be included with the mobile input tray to control a screen cursor on a display device and input data.

The mobile display system may be used to display medical information and to transmit data to the computer terminal. The computer transmits medical information such as x-ray image data to the mobile display system and the mobile display system displays the x-ray image data for a surgeon or medical practitioner to view. Sensor cameras mounted on the mobile display system sense movement of the surgeon's body and particular movements are identified as computer commands and transmitted to the computer terminal. To increase mobility of the mobile display system and decrease chances of violating a surgeon's sterile field through contact with power cables and communication cords, the mobile display system transmits data through wireless communication links and receives power from a portable power supply mounted on the mobile display system.

Wireless communications may also occur amongst and between the mobile input tray, the mobile display system, and the wireless headset in addition to wireless communication with the computer terminal. The wireless communications may use wireless communications standards such as WiFi and Bluetooth.

DETAILED DESCRIPTION OF THE INVENTION

Figure 1:
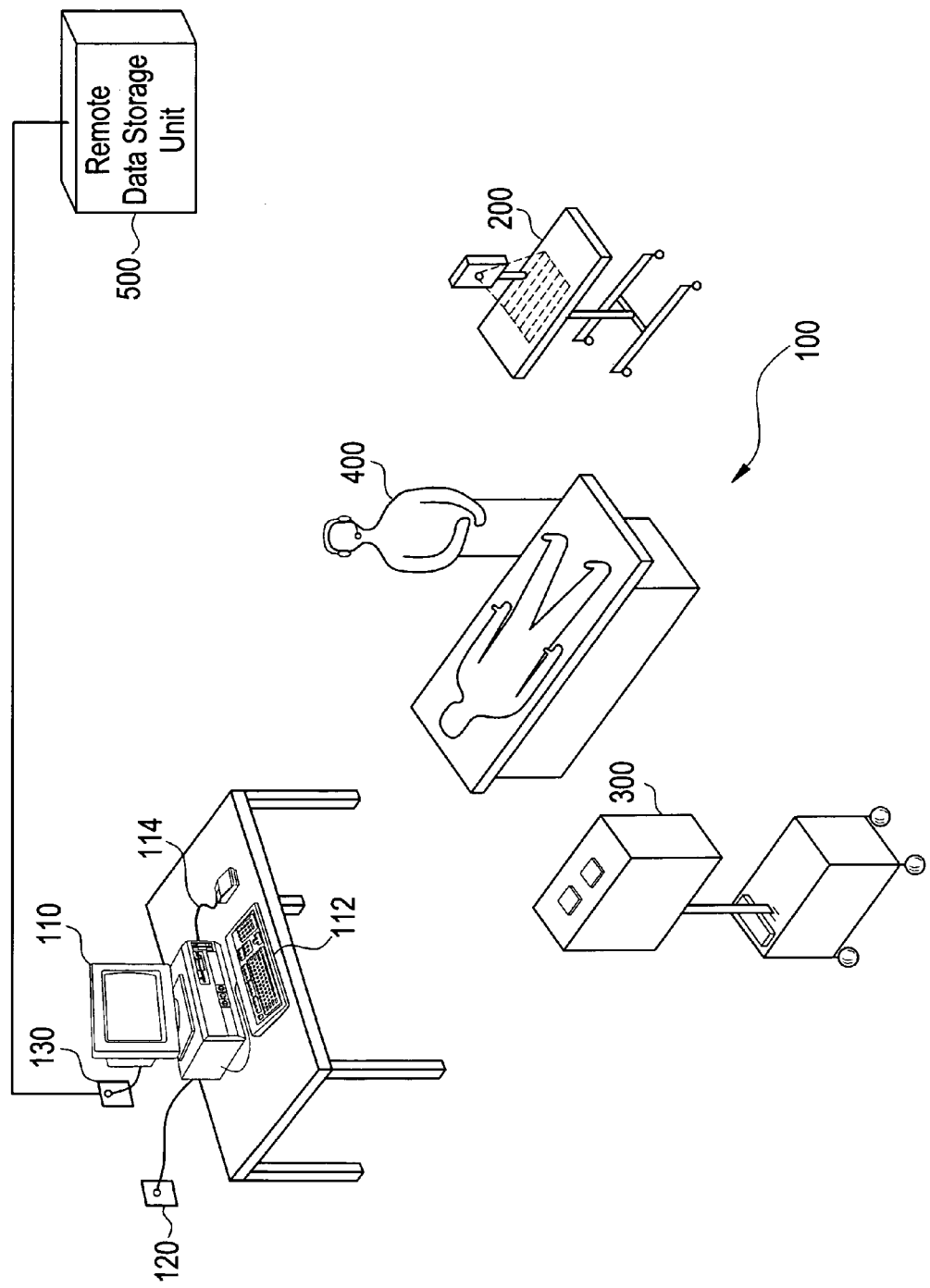
FIG. 1 illustrates a system for hygienic input of data for medical information systems in accordance with an embodiment of the present invention.

FIG. 1 illustrates an interactive medical system 100 for hygienic input of data into a medical information system in accordance with an embodiment of the present invention. The interactive medical system 100 includes local computer terminal 110, hard-wired keyboard 112, a hard-wired mouse 114, power outlet 120, data port 130, a wireless input tray 200, a wireless interactive visual display system 300, a wireless headset 400, and a remote data storage unit 500.

The remote data storage unit 500 stores patient medical information. The patient medical information may include medical data such as patient identifiers, images, lab results, medical diagnosis, and medical history. The remote data storage unit 500 transfers data to and from the local computer terminal 110 through the data port 130.

The local computer terminal 110 may be located within an operating room or in the vicinity of the operating room. The local computer terminal 110 is used by medical personnel to access the medical information stored in the remote data storage unit 500. The local computer terminal 110 plugs into and receives electrical power from the power outlet 120. The keyboard 112 and mouse 114 plug into local computer terminal 110. To access a patient's medical information and view medical data at the local computer terminal 110, medical personnel use their hands to manipulate the keyboard 112 and mouse 114 to control the local computer terminal 110. For example, information requests may be typed using the keyboard 112 or options may be selected on a screen by manipulating the mouse 114.

In addition to using the keyboard 112 or the mouse 114 to request patient medical information and enter new patient medical information, the wireless input tray 200, the wireless interactive visual display system 300, and the wireless headset 400 may be used. The wireless input tray 200, the wireless interactive visual display system 300, and the wireless headset 400 transfer data to and from the local computer terminal 110.

In operation, a surgeon may speak into the wireless headset 400 to request a patient's medical information. The wireless headset 400 transmits the surgeon's request to the local computer terminal 110. Communication between the wireless headset 400 and the local computer terminal 110 may use wireless communication standards such as the WiFi protocol or the Bluetooth standard. The local computer terminal 110 processes the request and accesses the remote data storage unit 500 to retrieve the requested data. After the requested data has been retrieved by the local computer terminal 110 from the remote data storage unit 500, the local computer terminal 110 transmits the requested data to an output device within the operating room.

In the interactive medical information system 100 of FIG. 1, the wireless headset 400 and the wireless interactive visual display system 300 may be used as output devices. If the requested data includes audio data, the audio data may be transmitted to either of the wireless headset 400 or the wireless interactive visual display system 300 for audio playback. If the requested data includes video data, the video data may be transmitted to the wireless interactive visual display system 300 for display.

The surgeon may also speak into the wireless headset 400 to add data to a patient's medical record or issue commands to the local computer terminal 110. The wireless headset 400 transmits the data or commands to the local computer terminal 110. The local computer terminal 110 then executes commands received from the wireless headset 400 and transmits data to the remote data storage unit 500 for storage with the patient's other medical information.

The surgeon may also transmit data to and request data from the local computer terminal 110 using the wireless input tray 200. To use the wireless input tray 200, the surgeon types textual data and commands on a keyboard on the wireless input tray 200 or manipulates a mouse on the wireless input tray 200. The wireless input tray 200 transmits the data to the local computer terminal 110. Communication between the wireless input tray 200 and the local computer terminal 110 may use wireless communication standards such as the WiFi protocol or the Bluetooth standard. The local computer terminal 110 then processes the data received from the wireless input tray 200 and accesses the remote data storage unit 500.

Preprogrammed hand gestures or other body motions of the surgeon may be detected by the wireless interactive visual display system 300 to enter data and request data from the local computer terminal 110. Sensors mounted on the wireless interactive visual display system 300 detect the surgeon's hand gestures and body motions. Depending upon which hand gesture or body motion is detected, the wireless interactive visual display system 300 commands the local computer terminal 110 to perform programmed tasks. Communication between the wireless interactive visual display system 300 and the local computer terminal 110 may use wireless communication standards such as the WiFi protocol or the Bluetooth standard.

Wireless communications may also occur amongst and between the wireless input tray 200, the wireless interactive visual display system 300, and the wireless headset 400 in addition to wireless communication with the computer terminal. For example, the wireless input tray 200 may transmit data such as keystrokes on the virtual keyboard to the wireless interactive visual display system 300. The wireless communications may use wireless communications standards such as WiFi and Bluetooth.

Figure 2:
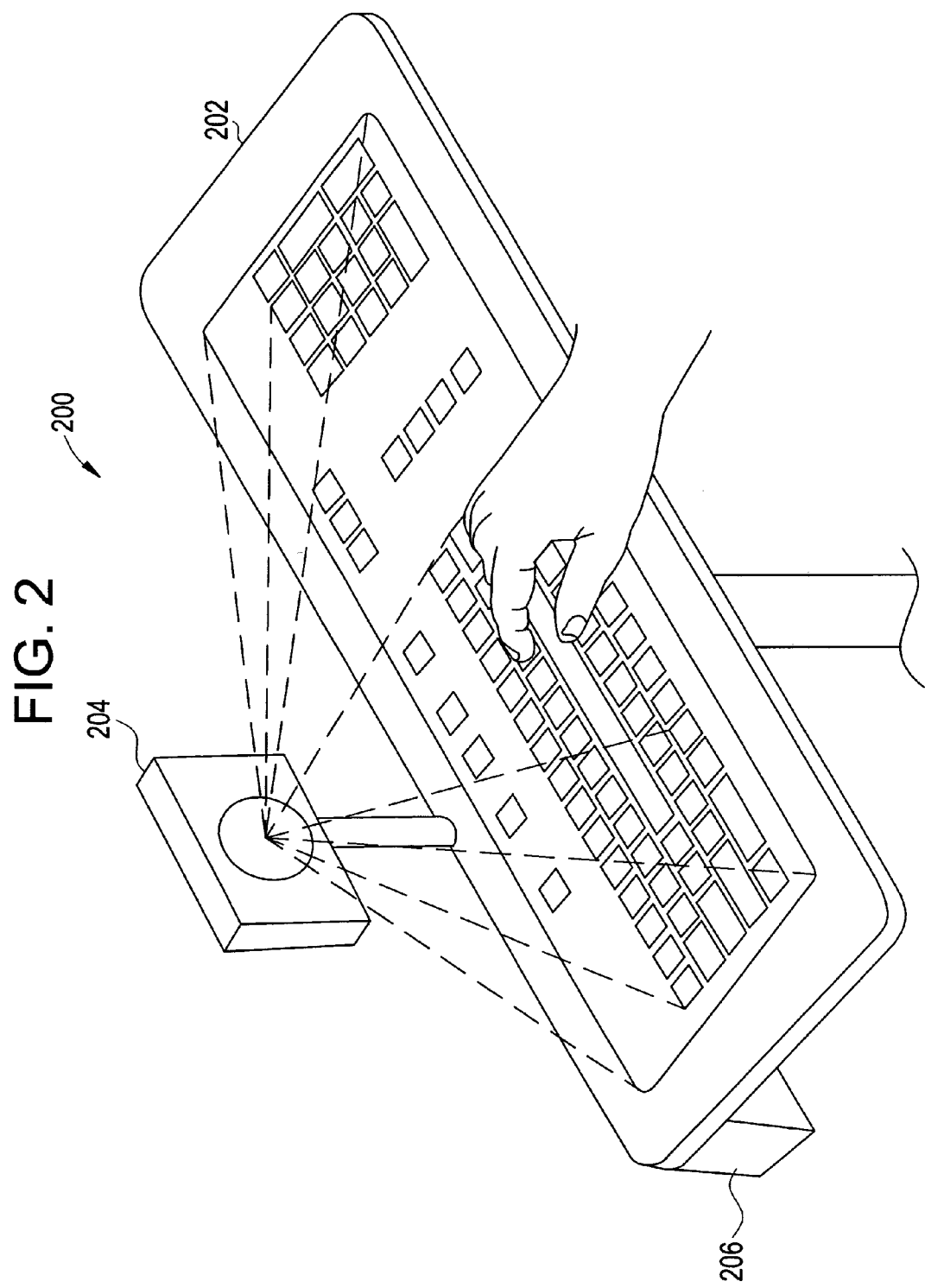
FIG. 2 illustrates a mobile wireless input tray for hygienic input of data for medical information systems in accordance with an embodiment of the present invention.

FIG. 2 illustrates an embodiment of the wireless input tray 200 of FIG. 1. The wireless input tray 200 includes a medical tray 202, a virtual keyboard projector 204, and a wireless tray communication device 206. The virtual keyboard projector 204 produces an optically generated image of a keyboard onto the top surface of the medical tray 202. To enter patient information or commands, the surgeon touches specific zones in the optically generated image.

For example, the optically generated image may resemble a typical "QWERTY" keyboard with the projected light forming symbols and closed boundaries around the symbols. Touching within the lighted boundary of a symbol is sensed by the virtual keyboard projector 204 and input of the corresponding symbol within the lighted boundary is registered. Data for the input symbol is then transmitted by the wireless tray communication device 206 to the local computer terminal 110.

Because the medical tray 202 may be sterilized, the wireless tray 200 may be positioned within the operating room near the surgeon during the procedure. When entering patient information or computer commands, the surgeon may touch the images projected on the medical tray 202 with little concern about having to re-scrub, re-glove, or re-sterilize hands that have touched the wireless input tray 200.

Figure 5:
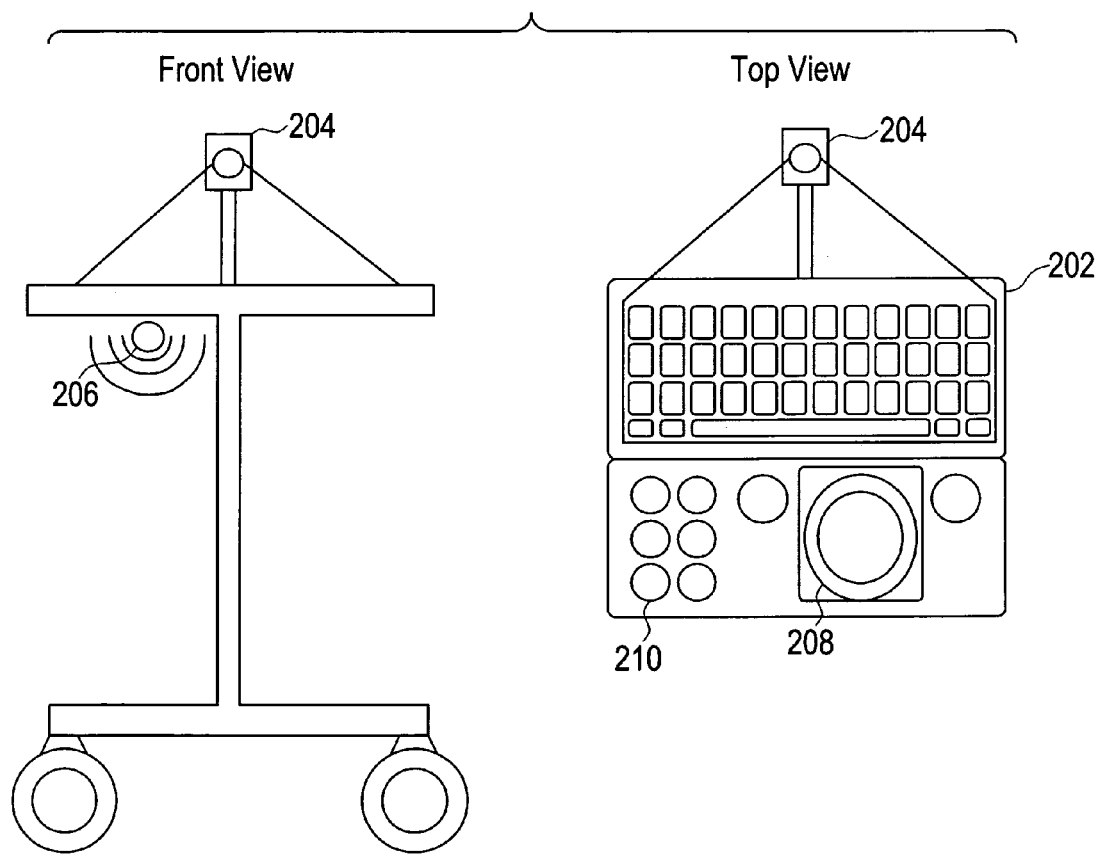
FIG. 5 illustrates an alternative embodiment for a mobile wireless input tray for hygienic input of data for medical information systems in accordance with an embodiment of the present invention.

In an alternative embodiment shown in FIG. 5, the wireless input tray 200 of FIG. 2 may include an operating room mouse 208. By using the operating room mouse 208, a surgeon may control a cursor on the local computer terminal 110 or the display of the wireless interactive visual display system 300. Buttons 210 may be positioned on or near the operating room mouse 208 to allow the surgeon to press the buttons 210 and execute specific repetitive tasks programmed for the buttons 210 via macros. The operating room mouse 208 may be designed to be fluid resistant and easy to sterilize in order to maintain the integrity of the surgeon's sterile field. An example of such an operating room mouse 208 is GE's 3D in room mouse.

Figure 3:
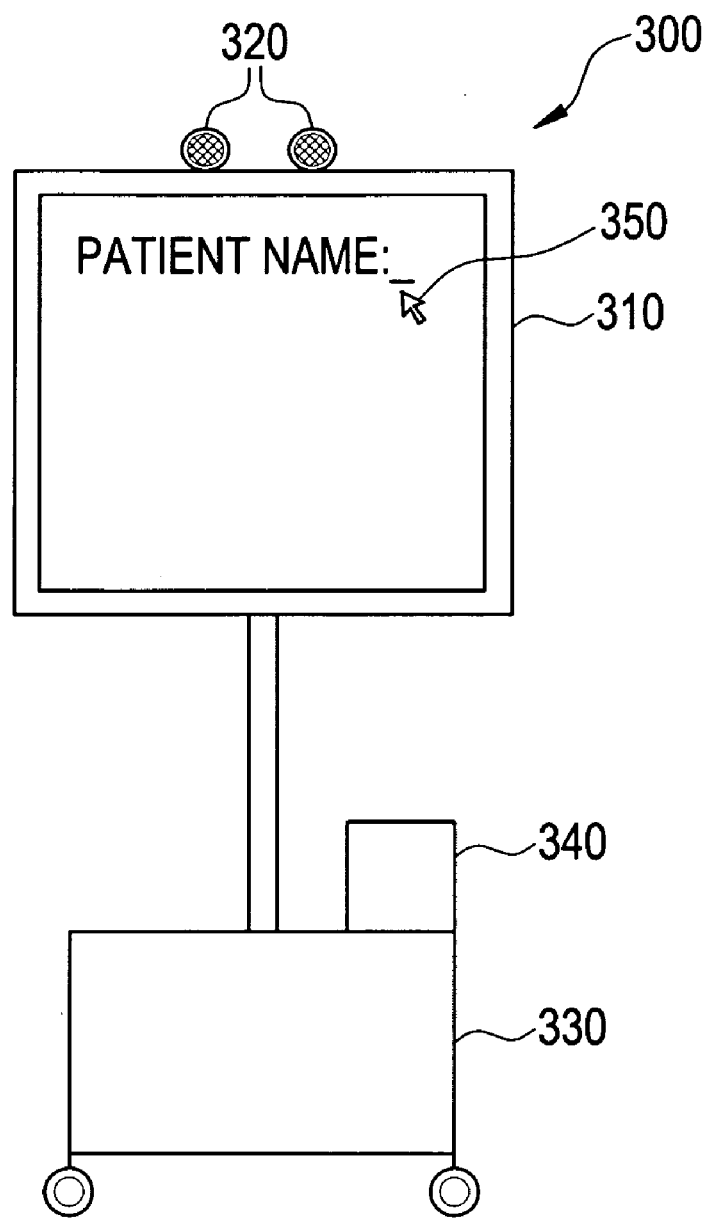
FIG. 3 illustrates a mobile wireless interactive visual display system for hygienic input of data for medical information systems in accordance with an embodiment of the present invention.

FIG. 3 illustrates an embodiment of the wireless interactive visual display system 300 of FIG. 1. The wireless interactive visual display system 300 includes a display monitor 310, sensor cameras 320, a mobile power supply 330, a wireless display communication device 340, and a screen cursor 350.

The wireless interactive visual display system 300 is a mobile system that may be positioned within the operating room during a procedure. Power for the wireless interactive visual display system 300 is provided by the mobile power supply 330. Communication between the wireless interactive visual display system 300 and the local computer terminal 110 is provided by the wireless display communication device 340. The wireless display communication device 340 receives display data from the local computer terminal 110. The display data is displayed on the display monitor 310.

The sensor cameras 320 detect movement and produce movement data. The movement data is transmitted to the local computer terminal 110 by the wireless display communication device 340.

In operation, the wireless interactive visual display system 300 may be positioned within the operating room. During a procedure, the surgeon views patient information on the display monitor 310 or enters new patient information. For example, the screen cursor 350 on the display monitor 310 may be manipulated by the surgeon during the procedure through preprogrammed hand movements or by using the wireless input tray 200.

If new patient information is entered using the wireless input tray 200, the patient information may be transmitted to the local computer terminal 110. The local computer terminal 110 then transmits the new patient information to the wireless interactive visual display system 300. The wireless display communication device 340 receives the data from the local computer terminal 110 and forwards the data for display on the display monitor 310.

If new patient information is entered using preprogrammed hand movements, or movement of other parts of the surgeon's body, the sensor cameras 320 may be used to sense the surgeon's movement and produce movement data. The movement data is then used to execute data requests and other commands. For example, a digital keyboard may be displayed on the display monitor 310. Side-to-side and up-down movement of the surgeon's right hand may control left-to-right and up-down movement of the screen cursor 350. Forward motion of the surgeon's right hand may be programmed to represent a data entry function whereby the keyboard symbol under the screen cursor 350 at the time of the forward hand motion is selected and entered. The entered data may then be transmitted to the local computer terminal 110 by the wireless display communication device 340.

Figure 4:
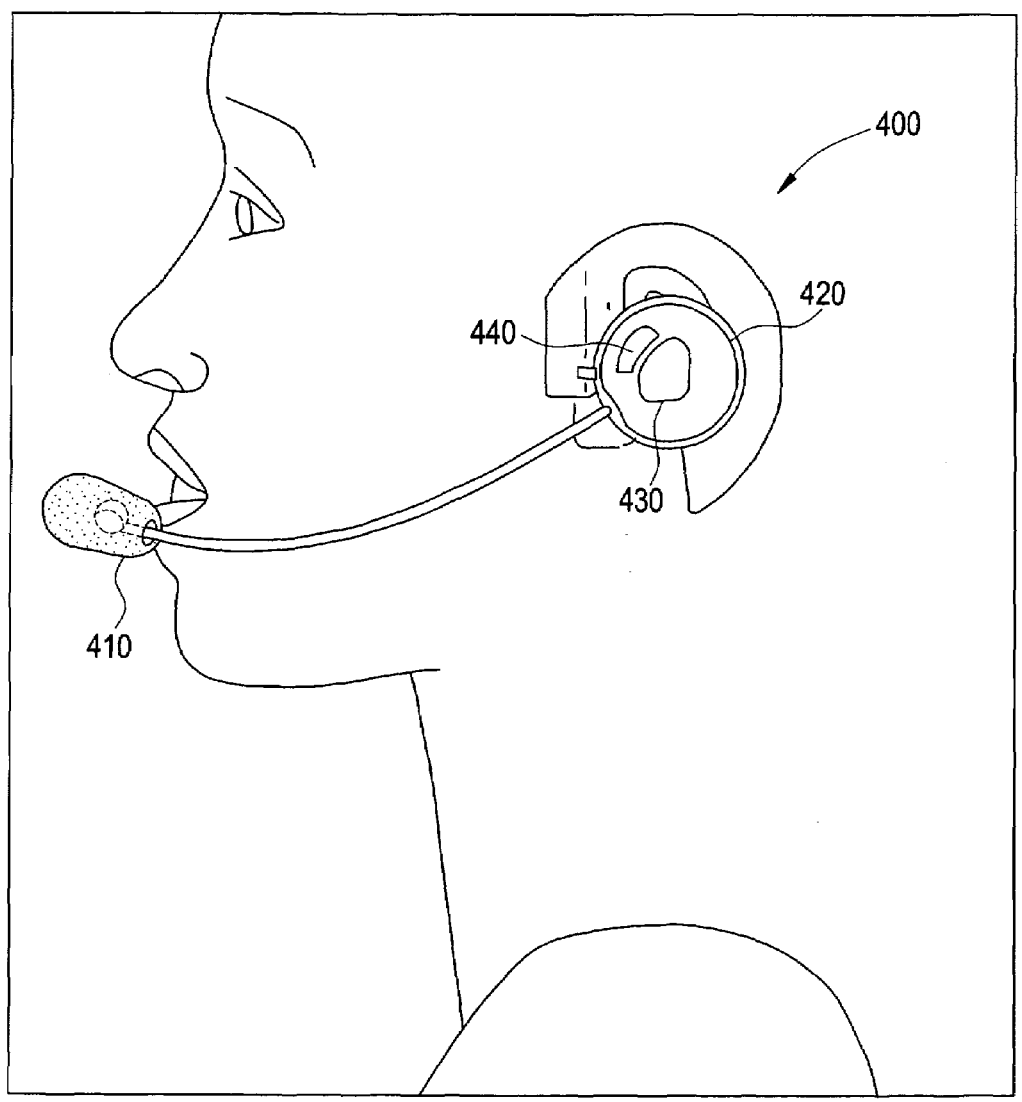
FIG. 4 illustrates a wireless headset for hygienic input of data for medical information systems in accordance with an embodiment of the present invention.

FIG. 4 illustrates an embodiment of the wireless headset 400 of FIG. 1. The wireless headset 400 includes a microphone 410, an audio earpiece 420, speakers 430, and a wireless headset communication device 440. A person using the wireless headset 400 speaks into the microphone 410 and listens to audio sounds through the speakers 430 in the audio earpiece 420.

In operation, the surgeon wears the wireless headset 400 within the operating room. The surgeon may request patient data, enter information about the current procedure, enter computer commands, and receive patient data using the wireless headset 400. To request patient data or enter computer commands, the surgeon speaks into the microphone 410. The request or command is transmitted from the wireless headset communication device 440 within the audio earpiece 420 of the wireless headset 400 to the local computer terminal 110. The local computer terminal 110 then executes commands received from the wireless headset communication device 440 within the wireless headset 400. If the surgeon requests patient information, the local computer terminal 110 accesses the remote data storage unit 500 and downloads the patient information. The local computer terminal 110 may then transmit the patient information to the wireless headset communication device 440 within the wireless headset 400 for playback through the speakers 430 in the audio earpiece 420 or the local computer terminal 110 may transmit the patient information to another output device such as the wireless interactive visual display system 300.

Thus, the wireless input tray 200, the wireless interactive visual display system 300, and the wireless headset 400 may be used in a system for hygienic input of medical information that preserve's the integrity of a surgeon's sterile field. For example, the wireless input tray 200, the wireless interactive visual display system 300, and the wireless headset 400 may be located within an operating room during a medical procedure.

Before the medical procedure, a surgeon may put on the wireless headset 400. The surgeon may then sterilize the surgeon's hands by scrubbing and putting on surgical gloves.

After the medical procedure has begun, the surgeon may desire to view existing patient medical information stored in the remote data storage unit 500 or enter new medical information obtained during the procedure. Rather than touch an unsterile computer keyboard 112 or unsterile mouse 114, which would require re-sterilizing the surgeon's hands by re-scrubbing and re-gloving, the surgeon may use the more hygienic input devices such as the wireless input tray 200, the wireless interactive visual display 300, or the wireless headset 400.

By using the wireless headset 400, the surgeon's sterilized hands do not contact an unsterile surface such as the computer keyboard 112 or computer mouse 114. The surgeon may speak requests and commands into the microphone 410 of the wireless headset 400. The wireless headset 400 then transmits the requests from the wireless headset communication device 440 to the local computer terminal 110. The local computer terminal 110 processes the requests and commands from the wireless headset communication device 440 in the wireless headset 400.

For example, the surgeon may request an x-ray image be displayed on the wireless interactive display system 300 and a radiologist's analysis of the x-ray image be played back through the audio earpiece 420 of the wireless headset 400. The local computer terminal 110 accesses the remote data storage unit 500 and downloads data for the requested x-ray image and audio data for the accompanying radiologist's analysis of the x-ray image. The local computer terminal 110 then transmits the data for the x-ray image to the wireless interactive visual display system 300. The wireless display communication device 340 of the wireless interactive visual display system 330 receives the transmitted data for the x-ray image. The wireless display communication device 340 forwards the x-ray image data to the display monitor 310 for display and viewing by the surgeon. The local computer terminal 110 also transmits audio data for the radiologist's analysis of the x-ray image to the wireless headset communication device 440 of the wireless headset 400. The wireless headset 400 receives the audio data and plays the audio data back through the speakers 430 in the audio earpiece 420 for listening by the surgeon.

Rather than touching the non-sterile keyboard 112 or mouse 114, the surgeon may enter patient information or computer commands using the wireless input tray 200. For example, the surgeon may type the patient's name and diagnostic information using a virtual keyboard projected on the wireless input tray 200. The wireless input tray 200 then transmits the information to the local computer terminal 110 for eventual storage. The surgeon may also use the wireless input tray 200 to control what is displayed on the screen of the display monitor 310 of the wireless interactive visual display system 300. To control what is displayed on the display monitor 310, the surgeon may type commands using the virtual keyboard of the wireless input tray 200 or manipulate the mouse 208 on the wireless input tray 200 to control the screen cursor 350.

The surgeon may also command and control what is displayed on the display monitor 310 with hand gestures and body motions. For example, the surgeon may move one of the surgeon's hands in the air to emulate the movements of a computer mouse. Side-to-side and up-down movement of the surgeon's hand may control left-to-right and up-down movement of the screen cursor 350. Forward motion of the surgeon's hand may be programmed to represent a data entry function whereby the keyboard symbol, folder icon, or file icon under the cursor at the time of the forward hand motion is selected. If the surgeon desires to access a specific patient file, the surgeon may search through file folders by selecting and opening various sub-folders until the appropriate patient file is reached. The desired file may then be selected and opened using pre-programmed hand gestures. The selected file may then be downloaded to the wireless interactive visual display system 300 for display on the display monitor 310.

Because the wireless input tray 200, wireless interactive visual display system 300, and the wireless headset 400 are not connected to power outlets and data ports with cables and wires during a medical procedure, the wireless input tray 200, wireless interactive visual display system 300, and the wireless headset 400 may be freely moved about the operating room without having to re-position power cords and communication wires. Also, medical personnel do not have to leave the operating room to use a local computer terminal in order to access patient medical information or contact unsterile devices such as a typical computer keyboard or a typical computer mouse. Consequently, the wireless headset 400, the wireless interactive visual display system 300, and the wireless tray 200 may be used for hygienic input of data without violating the sterile field of surgeons or other medical personnel.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A medical information system including:
   a mobile input tray;
   a computer terminal, wherein said mobile input tray transmits data to said computer terminal through a wireless communication link; and
   a headset, wherein said headset transmits data to said computer terminal through a wireless communication link.

2. A medical information system including:
   a mobile input tray;
   a computer terminal, wherein said mobile input tray transmits data to said computer terminal through a wireless communication link;
   a mobile display system, wherein said mobile display system receives medical information from said computer terminal through a wireless communication link and displays said medical information; and
   motion sensing cameras mounted on said mobile display system, wherein said motion sensing cameras detect motion of a medical information system user and transmit motion data associated with said motion to said local computer through said wireless communication link.

3. A method for transferring data in a medical information system including:
   providing a computer terminal, wherein said computer terminal provides access to medical information;
   transmitting data from a mobile input fray to said computer terminal through a wireless communication link; and
   transmitting data to said computer terminal from a headset, wherein said headset transmits data through a wireless communication link.

4. A method for transferring data in a medical information system including:
   providing a computer terminal, wherein said computer terminal provides access to medical information;
   transmitting data from a mobile input tray to said computer terminal through a wireless communication link;
   displaying medical information on a mobile display system, wherein said mobile display system receives medical information from said computer terminal through a wireless communication link;
   sensing motion of a medical information system user with motion sensing cameras mounted on said mobile display system; and
   transmitting motion data associated with said motion to said local computer through a wireless communication link.

* * * * *

UNITED STATES PATENT AND TRADEMARK OFFICE
CERTIFICATE OF CORRECTION

| | | |
|---|---|---|
| PATENT NO. | : 7,272,109 B2 | Page 1 of 1 |
| APPLICATION NO. | : 10/779235 | |
| DATED | : May 1, 2007 | |
| INVENTOR(S) | : Mark M. Morita, Steven L. Fors and Khal A. Rai | |

It is certified that error appears in the above-identified patent and that said Letters Patent is hereby corrected as shown below:

At col. 10, line 5, delete "fray" and insert --tray--

Signed and Sealed this

First Day of April, 2008

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,212,109 B2 |
| APPLICATION NO. | : 10/779235 |
| DATED | : May 1, 2007 |
| INVENTOR(S) | : Mark M. Morita, Steven L. Fors and Khal A. Rai |

It is certified that error appears in the above-identified patent and that said Letters Patent is hereby corrected as shown below:

At col. 10, line 5, delete "fray" and insert --tray--

Signed and Sealed this

Twenty-ninth Day of April, 2008

JON W. DUDAS
*Director of the United States Patent and Trademark Office*